United States Patent
Hong et al.

(10) Patent No.: US 10,125,073 B2
(45) Date of Patent: Nov. 13, 2018

(54) 2-METHOXY-4-(3-(4-METHOXYPHENYL) PROP-1-EN-1-YL)PHENOL AND PREPARATION METHOD THEREFOR

(71) Applicant: CHUNGBUK NATIONAL UNIVERSITY INDUSTRY—ACADEMIC COOPERATION FOUNDATION, Cheongju-si (KR)

(72) Inventors: Jin Tae Hong, Cheongju-si (KR); Hee Pom Lee, Cheongju-si (KR); Young Wan Ham, Orem, UT (US); Chun Sik Kim, Cheongju-si (KR); Heon Sang Jung, Cheongju-si (KR)

(73) Assignee: CHUNGBUK NATIONAL UNIVERSITY INDUSTRY-ACADEMIC COOPERATION FOUNDATION, Cheongju-si (KR)

( * ) Notice: Subject to any disclaimer, the term of this patent is extended or adjusted under 35 U.S.C. 154(b) by 0 days.

(21) Appl. No.: 15/556,060

(22) PCT Filed: Mar. 3, 2016

(86) PCT No.: PCT/KR2016/002124
§ 371 (c)(1),
(2) Date: Sep. 6, 2017

(87) PCT Pub. No.: WO2016/144042
PCT Pub. Date: Sep. 15, 2016

(65) Prior Publication Data
US 2018/0044275 A1    Feb. 15, 2018

(30) Foreign Application Priority Data
Mar. 6, 2015 (KR) ........................ 10-2015-0031372

(51) Int. Cl.
*C07C 43/23* (2006.01)
*C07C 41/30* (2006.01)

(52) U.S. Cl.
CPC .............. *C07C 43/23* (2013.01); *C07C 41/30* (2013.01)

(58) Field of Classification Search
CPC .................................. C07C 43/23; C07C 41/30
See application file for complete search history.

(56) References Cited

U.S. PATENT DOCUMENTS

2013/0316938 A1   11/2013   Baumgartner et al.

FOREIGN PATENT DOCUMENTS

KR    20120094308    8/2012

OTHER PUBLICATIONS

Pathak et al. ("Syntheses of 2-methoxyestradiol and eugenol template based diarylpropenes as non-steroidal anticancer agents", RSC Advances, vol. 4, Jul. 2014, pp. 35171-35185).*
International Search Report—PCT/KR2016/002124 dated Jul. 4, 2016.
Strych, et al., Biomimetic Synthesis of Santalin A,B and Santarubin A, B, the Major Colorants of Red Sandalwood, Angew, Chem. Int. Ed., 2013, vol. 52, pp. 9509-9512.
Veerareddy, et al., Synthesis of Entacapone by Pd-Catalyzed Heck Coupling Reaction, Synthetic Communications, 2014, pp. 1274-1278.
Ban, et al., Anti-arthritis effects of (E)-2,4-bis(p-hydroxyphenyl)-2-butenal are mediated by inhibition of the STAT3 pathway, British Journal of Pharmacology, 2014, pp. 2900-2912.
Boyle, et al., The JAK inhibitor tofacitinib suppresses synovial JAK1-STAT signalling in rheumatoid arthritis, Ann Rheum Dis, 2015, pp. 1311-1316.
Byun, et al., Epigallocatechin-3-gallate ameliorates both obesity and autoinflammatory arthritis aggravated by obesity by altering the balance among CD4+ T-cell subsets, Immunology Letters, 2014, pp. 51-59.
Ho, et al., Stat3 activation in urothelial stem cells leads to direct progression to invasive bladder cancer, Cancer Res., 2012, pp. 3135-3142.
Iliopoulos, et al., STAT3 Activation of miR-21 and miR-181b-1 via PTEN and CYLD Are Part of the Epigeneric Switch Linking Inflammation to Cancer, Molecular Cell, 2010, pp. 493-506.
Jhun, et al., Grape Seed Proanthocyanidin Extract-Mediated Regulation of STAT3 Proteins Contributes to Treg Differentiation and Attenuates Inflammation in a Murine Model of Obesity-Associated Arthritis, PLOS One, 2013, pp. 1-11.
Jhun, et al., Red Ginseng Extract Ameliorates Autoimmune Arthritis via regulation of STAT3 Pathway, TH17/Treg Balance, and Osteoclastogenesis in Mice and Human, Mediators of Inflammation, 2014, pp. 1-13.
Kim, et al., Effect of phloroglucinol on oxidative stress and inflammation, Food and Chemical Toxicology, 2010, pp. 2925-2833.
Kowluru, et al., Effects of curcumin on retinal oxidative stress and inflammation in diabetes, Nutrition & Metabolism, 2007.
Lee, et al., Interleukin-17 increases the expression of Toll-like receptor 3 via the STAT3 pathway in rheumatoid arthritis fibroblast-like synoviocytes, Immunology, 2013, pp. 353-361.

(Continued)

*Primary Examiner* — Rosalynd A Keys
(74) *Attorney, Agent, or Firm* — Cantor Colburn LLP

(57) ABSTRACT

Provided herein are 2-methoxy-4-(3-(4-methoxyphenyl) prop-1-en-1-yl)phenol having a novel structure capable of being used to prevent or treat all diseases associated with NF-κB, IKK and STAT3, and a method of preparing the same.

5 Claims, No Drawings

(56) References Cited

OTHER PUBLICATIONS

Park, et al., JAK2-STAT3 Blockade by AG490 Suppresses Autoimmune Arthritis in Mice via Reciprocal Regulation of Regulatory T Cells and TH17 Cells, The Journal of Immunology, 2014, pp. 4417-4424.

Ryu, et al., Treatment of IL-21R-Fc control autoimmune arthritis via suppression of STAT3 signal pathway mediated regulation of the Th17/Treg balance and plasma B cells, Immunology Letter, 2015, pp. 143-150.

Wu, et al., Evaluation and Discovery of Novel Synthetic Chalcone Derivatives as Anti-Inflammatory Agents, Journal of Chemistry, 2011, pp. 8110-8123.

Yang, et al., EGCG Attenuates Autoimmune Arthritis by Inhibition of STAT3 and HIF-1a with Th17/Treg Control, PLOS One, 2014, pp. 1-11.

Yu, et al., STATs in cancer inflammation and immunity: a leading role for STAT3, Nat Rev Cancer, 2009, pp. 798-809.

\* cited by examiner

2-METHOXY-4-(3-(4-METHOXYPHENYL)PROP-1-EN-1-YL)PHENOL AND PREPARATION METHOD THEREFOR

BACKGROUND

1. Technical Field

The present invention relates to 2-methoxy-4-(3-(4-methoxyphenyl)prop-1-en-1-yl)phenol having a novel structure and a method of preparing the same.

2. Description of the Related Art

NF-κB belongs to a protein family associated with inflammation modulation, immune modulation, apoptosis, cell proliferation, epithelial differentiation, etc., which regulates the expression of various genes and forms the backbone of an intracellular signaling pathway.

The understanding of the regulatory function in the inflammatory response and the immune system during the action of NF-κB offers new possibilities for the inflammatory response and immunotherapy after attempts to develop therapeutic agents using TNF-α inhibitors, and also the understanding of apoptosis and cell proliferation is important for research on the mechanisms of tumor development and metastasis. That is, it can be seen which genes are expressed by NF-κB in response to which external stimuli.

NF-κB is activated by inflammatory cytokines such as TNF-α interleukin-1 (IL-1), interleukin-6 (IL-6), GM-CSF, etc. Such activated NF-κB regulates the transcription of chemokines such as IL-8, macrophage-inflammatory protein (MIP)-1α, methyl accepting chemotaxis protein1 (MCP1), RANTES, eotaxin, etc.; adhesion molecules such as E-selectin, vascular cell adhesion molecule-1 (VCAM-1), endothelial leukocyte adhesion molecule 1 (ELAM1), intercellular cell adhesion molecule 1 (ICAM-1), etc.; inducible enzymes such as cyclooxygenase-2 (COX-2), inducible nitroxide synthase (iNOS), etc., as well as the cytokines. Therefore, it can be seen that the NF-κB is associated with almost all types of in vivo physiological responses.

For example, NF-κB serves to increase compounds associated with cell proliferation, apoptosis, and the cell cycle, as well as signal transduction substances in inflammation, the immune response, etc. Because the dysregulation of such an NF-κB activating pathway causes a continuous increase in such mediators, this condition is similar to autoimmune disorders. Also, NF-κB plays an important role in maintenance of oncogenic phenotypes by participating in the regulation of genes associated with cell proliferation and survival and genes associated with angiogenesis and metastasis. In effect, from the fact that NF-κB activity increased after anti-cancer treatments induces inhibition of apoptosis to reduce a therapeutic effect of anti-cancer drugs, the constitutive expression of NF-κB plays an important role in generation and treatment of tumors.

Also, NF-κB plays an important role in the inflammatory response by regulating genes encoding inducible enzymes such as pro-inflammatory cytokines, adhesion molecules, chemokines, growth factors, COX-2, or iNOS.

It has been found that the activity of NF-κB increases in epithelial carcinoma, carcinoma cell lines, lymphoma, etc., indicating that apoptosis is inhibited to increase a growth rate of cells and metastasis. In the case of the tumor in which NF-κB is activated, it is known that the tumor does not react well to anti-cancer drugs because P-glycoprotein inducing multi-drug resistance is considered to be encoded by a gene regulated by NF-κB. On the other hand, the inhibition of NF-κB activation in fibrosarcoma or colorectal cancer cell lines creates an environment in which apoptosis may be easily induced, resulting in favorable outcomes for radiotherapy or anti-cancer therapy. NF-κB activation causes growth of blood vessels through vascular endothelial growth factors (VEGFs), COX-2, and iNOS, and plays part in invasion and metastasis of tumors through matrix metalloproteinases, plasminogen activators, heparinases, etc.

NF-κB may be regulated at multiple steps, and thus the prevention and treatment of various diseases may be accomplished by inhibiting NF-κB activation.

For example, immune cells participate in inflammation or the immune response due to the production of ROS, NO and PGE2. In this case, as a redox-sensitive transcription factor, NF-κB is activated by oxidative stress and inflammatory mediators to play an important role in inflammatory diseases. The activity of NF-κB is mediated by IκB kinases (IKKs) through oxidative and anti-inflammatory stress. This is because NF-κB and/or IKKs are/is suitable as a target of an anti-inflammatory drug having an anti-oxidative activity. Also, various antioxidants such as gravinol, phloroglucinol, pycnogenol, and curcumin have an anti-inflammatory effect through the inactivation of IKKs and/or NF-κB.

By way of example, the present inventors have proposed that 2,4-bis(p-hydroxyphenyl)-2-butenal induces inactivation of NF-κB, and thus may be used as a medicine having an anti-inflammatory or anti-arthritic effect, as disclosed in Korean Patent Unexamined Publication No. 2012-0094308.

In addition, the use of various compounds has been suggested in connection with the control of NF-κB activity.

As a proanthocyanidin extracted from grape seeds, gravinol blocks nuclear transfer of NF-κB in intestinal epithelia induced by high glucose, and thus may be used as a potent anti-oxidative or anti-inflammatory agent. Also, it is known that phloroglucinol which is a monomer of phlorotannins in brown alga has an antioxidant activity of promoting anti-oxidative gene expression and anti-inflammatory activity of hindering NF-κB and IKK activities (Kim M M, Kim S K. Effect of phloroglucinol on oxidative stress and inflammation. *Food Chem Toxicol.* 48(10): pp 2925-33 (2010)).

Further, it is also known that curcumin hinders oxidative stress and inflammation in the retina through inactivation of NF-κB in diabetic patients (Kowluru R A, Kanwar M. Effects of curcumin on retinal oxidative stress and inflammation in diabetes. *Nutr Metab* (Lond). 16; 4: 8 (2007)).

Meanwhile, in addition to NF-κB, signal transducer and activator of transcription 3 (STAT3) is an important transcription factor associated with inflammatory and immune responses.

STAT3 is a protein that remains inactivated in the cytoplasm, binds to a DNA base sequence as a part of a group referred to as a 'DNA binding factor,' and serves to regulate a transcription process in which genetic information in DNA is transferred to RNA strands.

Accordingly, STAT3 participates in the immune response as well as the inflammatory response to play a pivotal role in connection with arthritis or cancer.

In connection with the inflammatory response, STAT3 is a factor that plays a critical role in IL-6-induced synovial infiltration in inflammatory arthritis and is important in directly regulating the expression of oxidants or inflammatory mediators such as NO, iNOS, COX-2, IL-6, IL-1, etc. Activation of STAT3 occurs by phosphorylating a tyrosine residue in a STAT3 transactivation domain by means of various growth factors and cytokines. Such phosphorylated STAT3 (p-STAT3) enters the nuclei to induce expression of a wide range of target genes associated with the inflammatory response and tumorigenesis.

In particular, STAT3 is an important transcription factor that interacts with NF-kB and participates in inflammation and the immune response. Therefore, the STAT3 forms a complex with p65 of NF-kB serving to inhibit the transcriptional activity of an iNOS gene to mediate a physical/functional interaction with NF-kB, and then stimulates cells together with the inflammatory mediators and cytokines. Once such NF-kB and STAT3 are activated, they regulate expression of anti-apoptotic, proliferation-promoting and immune response genes.

Thus, Jianzhang Wu et al. suggested that chalcone derivatives may be used to treat various inflammatory diseases because the chalcone derivatives suppress cytokines such as IL-6 and tumor necrosis factors [Jianzhang Wu et al., Evaluation and Discovery of Novel Synthetic Chalcone Derivatives as Anti-Inflammatory Agents, *J. Med. Chem.* 2011, 54, 8110-8123].

Also, STAT3 is associated with an arthritis development mechanism, and arthritis may be treated and prevented by suppressing the activation of STAT3.

Rheumatoid arthritis is a chronic autoimmune disorder characterized by inflammation of the lining, or synovium, of the joints. Thus, rheumatoid arthritis is a systemic autoimmune disorder caused by chronic joint inflammation. It is known that the STAT3 activation plays an important role in development of rheumatoid arthritis, and various anti-inflammatory substances such as melittin, and the like suppress the development of rheumatoid arthritis in a way to hinder STAT3 activation [Jung Ok Ban et al., Anti-arthritis effects of (E)-2,4-bis(p-hydroxyphenyl)-2-butenal are mediated by inhibition of the STAT3 pathway].

In the case of IL-21 as a T cell-induced cytokine regulating T cells, B cells, and NK cells, an increase in level of IL-21 causes a decrease in phosphorylation of STAT3, resulting in clinically and histologically relieved symptoms of autoimmune arthritis. Using this fact, research has been conducted to apply IL-21 to treat rheumatoid arthritis [Ryu J G et al., Treatment of IL-21R-Fc control autoimmune arthritis via suppression of STAT3 signal pathway-mediated regulation of the Th17/Treg balance and plasma B cells, Immunol Lett. 2015 February; 163(2): 143-50].

In recent years, when tofacitinib, which is an oral JAK inhibitor, is administered as an arthritis therapeutic agent to patients with rheumatoid arthritis, an expression level of metalloproteinase and interferon regulatory genes is remarkably reduced in the synovium of the rheumatoid arthritis patients. It is suggested that such a JAK inhibitor has a clinical improvement effect on decreased STAT3 phosphorylation [Boyle D L et al., The JAK inhibitor tofacitinib suppresses synovial JAK1-STAT signaling in rheumatoid arthritis, Ann Rheum Dis. 2014 Nov. 14].

In addition, Jhun et al. reported that a red *Panax Ginseng* root extract has a therapeutic effect on arthritis by stimulating Treg cells and reducing the number of Th17 cells due to a remarkable decrease in STAT3 phosphorylation in autoimmune diseases [Jhun J et al., 1 Red *ginseng* extract ameliorates autoimmune arthritis via regulation of STAT3 pathway, Th17/Treg balance, and osteoclastogenesis in mice and humans, *Mediators Inflamm.* 2014; 2014: 351856].

IL-17 is a cytokine that increases expression of synovial toll-like receptors (TLRs) to have an influence on the innate immune system, and thus is a factor important for the onset of rheumatoid arthritis. As a result of examining an effect of IL-17 on expression of the toll-like receptors (TLRs) in fibroblast-like synoviocytes (FLSs) of patients with osteoarthritis and rheumatoid arthritis, it was found that STAT3 blockade reduces the TLR3 expression caused by IL-17 induction, indicating that the TLR3 expression may be regulated under the control of a STAT3 pathway in rheumatoid arthritis [Seon-Yeong Lee et al., Interleukin-17 increases the expression of Toll-like receptor 3 via the STAT3 pathway in rheumatoid arthritis fibroblast-like synoviocytes, *Immunology*, Volume 141, Issue 3, pages 353~361, March 2014].

In addition, IL-6-mediated STAT3 signals are essential for Th17 differentiation, and play a pivotal role in the onset of rheumatoid arthritis. An inhibitory effect on rheumatoid arthritis and an effect on T cell modulation through the STAT3 inhibition using a JAK2 inhibitor were examined. As a result, it was found that, when the JAK2 inhibitor is administered, a level of STAT3 phosphorylation is lowered, the expression of Treg-related molecules is increased, and the function and development of osteoclasts are suppressed, indicating that the control of a JAK2/STAT3 pathway is very useful in treating rheumatoid arthritis [Park J S et al., JAK2-STAT3 blockade by AG490 suppresses autoimmune arthritis in mice via reciprocal regulation of regulatory T Cells and Th17 cells, *J Immunol.* 2014 May 1; 192(9): 4417-24].

Further, epigallocatechin-3-gallate (EGCG) in green tea (*Camellia sinensis*) polyphenol is a type of catechin that has the highest biological activity in green tea, and serves to enhance potent anti-oxidative and anti-inflammatory effects by means of inhibition of signaling and gene expression. Therefore, Yang E J et al. conducted various types of research to investigate whether EGCG relieves arthritis and prevents articular destruction, remarkably reduces STAT3 phosphorylation and thus expression of Th17 cell and osteoclast markers, and hinders the activity of osteoclasts, and suggested that the EGCG may be used as a potent therapeutic agent against autoimmune arthritis [Yang E J et al., EGCG attenuates autoimmune arthritis by inhibition of STAT3 and HIF-1α with Th17/Treg control. *PLoS One.* 2014 Feb. 18; 9(2): e86062].

Also, EGCG has a therapeutic effect on autoinflammatory diseases and obesity. That is, EGCG serves to reduce weight and lower fat infiltration in the liver tissue by inhibiting expression of STAT3 proteins and differentiation of Th17 cells and improve arthritis and various inflammatory indexes [Byun J K et al., Epigallocatechin-3-gallate ameliorates both obesity and autoinflammatory arthritis aggravated by obesity by altering the balance among CD4+ T-cell subsets, Immunol Lett. 2014 January-February; 157(1-2): 51-9].

In addition, as a substance extracted from the grape seeds, proanthocyanidin (GSPE) is a natural flavonoid that enhances an anti-inflammatory property. Obesity is caused by secretions of inflammatory cells and pre-inflammatory molecules in an inflammatory condition. Administration of GSPE significantly controls weight gain, lowers fat infiltration in the liver, and improves blood circulation. An anti-obesity effect of GSPE results from an increase in the number of Treg cells and a decrease in the number of Th17 cells. In this case, the decrease in the number of Th17 cells is associated with the definite inhibition of phosphorylation of STAT3 as a main transcription factor. That is, the GSPE may be used to treat immune diseases caused by STAT3 hyperactivity, such as autoimmune diseases and metabolic disorders, by inhibiting STAT3 activity [Jhun J Y et al, Grape seed proanthocyanidin extract-mediated regulation of STAT3 proteins contributes to Treg differentiation and attenuates inflammation in metabolic disorders a murine model of obesity-associated arthritis, *PLoS One*. 2013 Nov. 5; 8(11): e78843].

IL-23 is a novel cytokine that targets CD4(+) T cells serving to indirectly promote differentiation of osteoclast precursors by increasing the release of IL-17 from the CD4(+) T cells. In this case, IL-17 serves to promote formation of osteoclasts from osteoclast precursor cells. Also, IL-23 enhances the receptor activity of NF-kB to contribute to osteoclast formation. In this case, it has been found that this pathway is mediated by NF-KB and STAT3. In the future, IL-23 mediating STAT3 phosphorylation is expected to be a promising target in treating bone destruction associated with arthritis.

In addition to the relationship between STAT3 and arthritis, STAT3 also has an influence on the mechanisms of cancer development and treatment.

That is, STAT proteins serve to equally regulate the inflammatory response and immunologic action caused by cytokines. In particular, the STAT proteins play a central role in determining whether or not to promote the immune response or to inhibit cancer in a tumor environment [Yu H et al, STATs in cancer inflammation and immunity: a leading role for STAT3, *Nat Rev Cancer*. 2009 November; 9(11): 798-809].

Because STAT3 is only a molecule that regulates genes associated with the onset and promotion of cancer, STAT3 acts as the first step in cancer onset/progression processes. Also, STAT3 may be a signal transduction activating factor which leads to cancer by inappropriately sending external signals to differentiate healthy cells because the role of STAT3 as a transcription factor protein is associated with tumorigenesis in addition to wound healing.

Yu H et al. suggests that the persistent activity of STAT3 mediates the inflammatory response which promotes tumors, and thus constitutively activated STAT3 and some STATS increase growth, survival and invasion of tumor cells while suppressing an anti-tumor immune action.

That is, transient inflammatory signals activate an epigenetic switch to convert untransformed cells into cancer cells via a positive feedback loop such as NF-kB, Lin28, Let-7, IL-6, etc. In this case, STAT3 transcription factors activated by IL-6 serves to directly activate microRNAs, such as miR-21 and miR-181b-1, which inhibit phosphatase and tensin homolog (PTEN) and cylindromatosis (CYLD) tumor suppressors, to induce an increase in activity of NF-kB. That is, it is STAT3 that plays a role as a part of a positive feedback loop, which underlies the epigenetic switch linking inflammation to cancer, via the cytokines such as miR-21, miR-181b-1, PTEN, and CYLD [Iliopoulos D et al., STAT3 activation of miR-21 and miR-181b-1 via PTEN and CYLD are part of the epigenetic switch linking inflammation to cancer, *Mol Cell*. 2010 Aug. 27; 39(4): 493-506.4].

In addition, STAT3 is constitutively activated in a wide range of tumors including colon cancer, liver cancer, breast cancer, prostate cancer, multiple myeloma, and glioblastoma because tumor cells are dependent on STAT3 to sustain their growth and avoid apoptosis.

STAT3 activation plays an important role in a variation in saccharolytic energy and blood glucose dependence of tumor cells. This is because STAT3 regulates expression of Akt, and Akt is a regulatory factor responsible for the upregulation of HIF-1. In this case, it may be because STAT3 plays an important role in expression of hypoxia-inducible factor-1 (HIF-1) as a master transcriptional regulatory factor that regulates the genomic response induced in a hypoxic state.

Also, in the pathways through which two subtypes of human bladder cancer, that is, non-invasive papillary and muscle-invasive cancer, develop, the expansion of stem cells induced by STAT3 plays a pivotal role in clinical progression of invasive bladder cancer through a carcinoma in situ (CIS) pathway. That is, it was reported that, when the STAT3 is constitutively activated, a carcinogen BBN induces urothelial precursor cells to promote CIS formation and rapidly develop into muscle-invasive cancer. STAT3 plays an important role in urothelial basal cells leading to new CIS formation and development into invasive cancer [The role of STAT3 activation in invasive bladder cancer, Abstract from the Global Trend Briefing by the KISTI MIRIAN, 2012-07-26].

Also, STAT3 plays an important role in development of skin cancer. That is, because STAT3 plays a dual role in tumor inflammatory response and immunologic action, the technology of suppressing STAT3 expression in cancer treatments may be an approach having a high potential for treatment of cancer and inflammation. Accordingly, an STAT3 inhibitor may be used as a topical cream for treating burned skin or precancerous wounds so that the burned skin or precancerous wounds do not develop into cancer.

As described above, it can be seen that the inhibition of STAT3 activity may be one alternative to effectively treat the variety of aforementioned diseases because STAT3 is variously associated with the development and growth of arthritis and cancer as well as the inflammatory response.

PRIOR-ART DOCUMENTS

Patent Documents

Patent Document 1: Korean Patent Publication No. 2012-0094308

Non-Patent Documents

Non-patent Document 1: Jianzhang Wu et al., Evaluation and Discovery of Novel Synthetic Chalcone Derivatives as Anti-Inflammatory Agents, J. Med. Chem. 2011, 54, 8110-8123

Non-patent Document 2: Jung Ok Ban et al., Anti-arthritis effects of (E)-2,4-bis(p-hydroxyphenyl)-2-butenal are mediated by inhibition of the STAT3 pathway STAT3 protein could lead to new ways to prevent skin cancer, Published on Nov. 4, 2004

Non-patent Document 3: Ryu J G et al., Treatment of IL-21R-Fc control autoimmune arthritis via suppression of STAT3 signal pathway-mediated regulation of the Th17/Treg balance and plasma B cells, Immunol Lett. 2015 February; 163(2): 143-50

Non-patent Document 4: Boyle D L et al., The JAK inhibitor tofacitinib suppresses synovial JAK1-STAT signaling in rheumatoid arthritis, Ann Rheum Dis. 2014 Nov. 14

Non-patent Document 5: Jhun J et al., 1 Red *ginseng* extract ameliorates autoimmune arthritis via regulation of STAT3 pathway, Th17/Treg balance, and osteoclastogenesis in mice and humans, Mediators Inflamm. 2014; 2014: 351856.

Non-patent Document 6: Seon-Yeong Lee et al., Interleukin-17 increases the expression of Toll-like receptor 3 via the STAT3 pathway in rheumatoid arthritis fibroblast-like synoviocytes. Immunology, Volume 141, Issue 3, pages 353~361, March 2014

Non-patent Document 7: Park J S et al., JAK2-STAT3 blockade by AG490 suppresses autoimmune arthritis in mice via reciprocal regulation of regulatory T Cells and Th17 cells, J Immunol. 2014 May 1; 192(9): 4417-24

Non-patent Document 8: Yang E J et al., EGCG attenuates autoimmune arthritis by inhibition of STAT3 and HIF-1α with Th17/Treg control. PLoS One, 2014 Feb. 18; 9(2): e86062

Non-patent Document 9: Byun J K et al., Epigallocatechin-3-gallate ameliorates both obesity and autoinflammatory arthritis aggravated by obesity by altering the balance among CD4+ T-cell subsets, Immunol Lett. 2014 January-February; 157(1-2): 51-9

Non-patent Document 10: Jhun J Y et al., Grape seed proanthocyanidin extract-mediated regulation of STAT3 proteins contributes to Treg differentiation and attenuates inflammation in a murine model of obesity-associated arthritis, PLoS One. 2013 Nov. 5; 8(11): e78843

Non-patent Document 11: Yu H et al, STATs in cancer inflammation and immunity: a leading role for STAT3, Nat Rev Cancer. 2009 November; 9(11): 798-809

Non-patent Document 12: Iliopoulos D et al., STAT3 activation of miR-21 and miR-181b-1 via PTEN and CYLD are part of the epigenetic switch linking inflammation to cancer, Mol Cell. 2010 Aug. 27; 39(4): 493-506.4

Non-patent Document 13: The role of Stat3 activation in invasive bladder cancer, Abstract from the Global Trend Briefing by the KISTI MIRIAN, 2012-07-26

SUMMARY

Therefore, the present inventors have conducted research in various aspects to prepare a novel compound in order to control the activities associated with NF-κB, IKK and STAT3, and prepared a compound having a novel structure through the Heck reaction.

Accordingly, it is an aspect of the present invention to provide a compound having a novel structure, and a method of preparing the same.

To solve the above problems, according to one aspect of the present invention, there is provided 2-methoxy-4-(3-(4-methoxyphenyl)prop-1-en-1-yl)phenol represented by the following Formula 1:

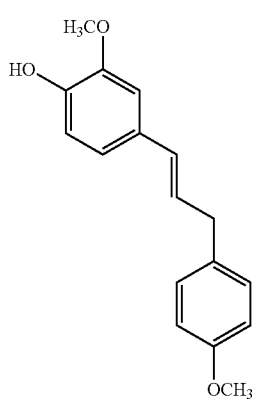

[Formula 1]

According to another aspect of the present invention, there is provided a method of preparing 2-methoxy-4-(3-(4-methoxyphenyl)prop-1-en-1-yl)phenol of Formula 1, which is prepared by allowing a compound of Formula 2 to react with a compound of Formula 3, as represented by the following Scheme 1:

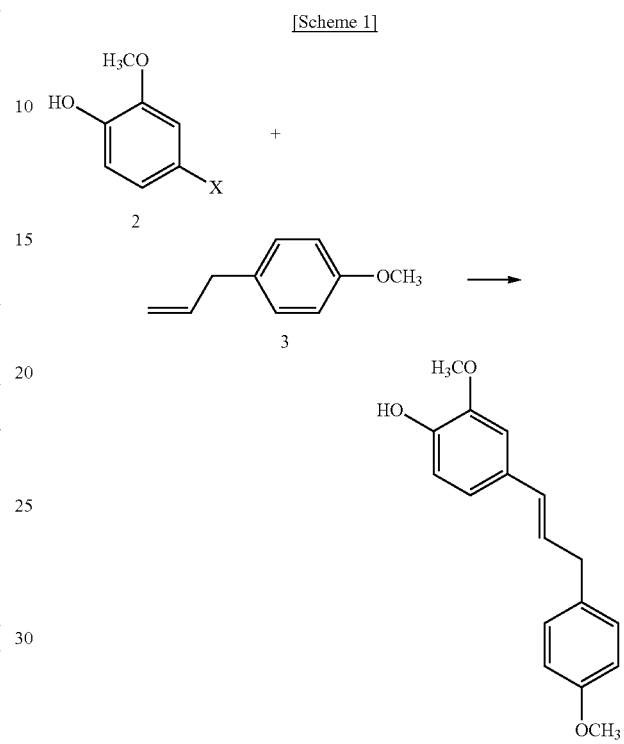

[Scheme 1]

wherein X is a halogen element.

DETAILED DESCRIPTION OF EMBODIMENTS

According to the present invention, a novel compound represented by the following Formula 1 is provided.

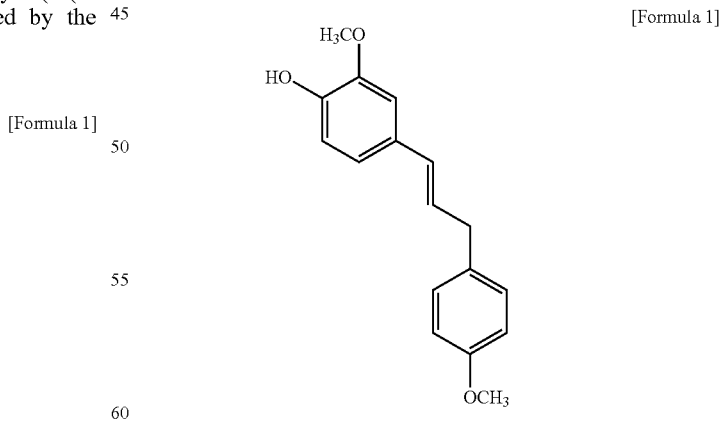

[Formula 1]

The compound is named 2-methoxy-4-(3-(4-methoxyphenyl)prop-1-en-1-yl)phenol (hereinafter referred to as 'MMPP'), and has a molecular formula of $C_{17}H_{18}O_3$ and a molecular weight of 270.3 g/cm$^3$.

The MMPP includes optical isomers, stereoisomers, polymorphs, racemic mixtures, solvates, hydrates, metabolites, and pharmaceutically acceptable salts thereof. Preferably, the MMPP may be (E)-2-methoxy-4-(3-(4-methoxyphenyl)prop-1-en-1-yl)phenol.

The MMPP provided in the present invention may be prepared using various methods. For example, the MMPP may be prepared through the Heck reaction.

The Heck reaction is a coupling reaction using palladium as a catalyst, that is, a reaction in which a compound having an unsaturated group is prepared in a one-step reaction by attaching an aromatic or olefinic group to an alkene.

Specifically, as represented by Scheme 1, the MMPP represented by Formula 1 is prepared by allowing a compound of Formula 2 to react with a compound of Formula 3:

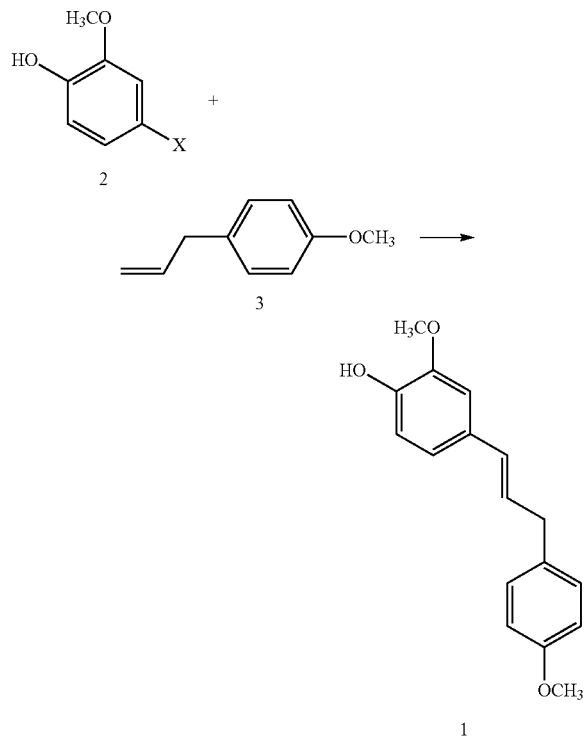

[Scheme 1]

wherein X is a halogen element.

Preferably, X is F, Cl, I, or Br. More preferably, I or Br has the highest reactivity.

In Scheme 1, any compound may be used as long as the compound of Formula 2 is a methoxyphenol derivative and may satisfy X. This reactant may be prepared directly, or commercially available reactants may be purchased and used herein. According to one exemplary embodiment of the present invention, 4-iodo-2-methoxyphenol is used.

Also, the compound of Formula 3 may be prepared directly, or commercially available compounds may be purchased and used herein.

Scheme 1 may be carried out in the presence of a palladium catalyst and a base, and a ligand may be added to enhance reactivity.

Any palladium catalyst may be used as long as the palladium catalysts are used in a known coupling reaction, but the present invention is not particularly limited thereto. Representatively, the palladium catalyst may include one or more selected from the group consisting of tris(dibenzylideneacetone)dipalladium ($Pd_2(dba)_3$), tetrakis(triphenylphosphine)palladium ($Pd(PPh_3)_4$), bis(triphenylphosphine)palladium chloride ($Pd(PPh_3)_2Cl_2$), bis(acetonitrile)palladium (II) chloride ($Pd(CH_3CN)_2Cl_2$), palladium (II) acetate ($Pd(OAc)_2$), palladium (II) acetylacetonate ($Pd(acac)_2$), an allylpalladium (II) chloride dimer ($Pd(allyl)Cl)_2$), palladium on carbon (Pd/C), and palladium (II) chloride ($PdCl_2$). According to one exemplary embodiment of the present invention, $Pd(OAc)_2$ is used.

As a reaction accelerator, the base, for example, includes an organic or inorganic salt such as potassium chloride, potassium bromide, potassium iodide, sodium chloride, sodium bromide, sodium iodide, ammonium chloride, ammonium bromide, ammonium iodide, ammonium tetra-n-butyl bromide, phosphinium tetra-n-butyl bromide, ammonium benzyltriethyl chloride, or ammonium benzyltriethyl bromide, an organic or inorganic acid such as formic acid, acetic acid, propionic acid, carbonic acid, carbon dioxide, hydrogen chloride, hydrogen bromide, or hydrogen iodide, and an organic or inorganic base such triethylamine, tributylamine, dimethylaniline, pyridine, sodium hydroxide, potassium hydroxide, sodium hydride, and potassium hydride. According to one exemplary embodiment of the present invention, tributylamine is used.

Such a base is used at a content of 0.1 to 1,000% mole, preferably 1 to 200% mole, based on one mole of the palladium catalyst.

In Scheme 1, the reaction may be carried out with high yield within a short time by adding a ligand to further promote the reaction, when necessary.

For example, a phosphorus compound, an arsenic compound, an antimony compound, a diene compound, and a diketone compound are used as the ligand. Preferably, a phosphine or phosphite is used as the phosphorus compound.

For example, the phosphine includes an alkylphosphine such as triethylphosphine, tri-n-propylphosphine, tri-i-propylphosphine, or tri-n-butylphosphine, and a triarylphosphine such as triphenylphosphine For example, the phosphite includes an alkyl phosphite such as triethyl phosphite, tri-n-propyl phosphite, tri-i-propyl phosphite, or tri-n-butyl phosphite, and a triarylphosphite such as triphenylphosphite.

According to one exemplary embodiment of the present invention, triphenylphosphine is used.

Such a ligand is used at a content of 0.01 to 500% mole, preferably 3 to 300% mole, based on one mole of the palladium catalyst.

This reaction may be carried out without a solvent, but the solvent may be used when necessary.

The solvent may be an ether solvent such as diethyl ether, tetrahydrofuran, 1,4-dioxane, ethylene glycol diethyl ether, dimethoxyethane, bis(2-methoxyethyl)ether, diethylene glycol diethyl ether, or anisol, an aromatic solvent such as benzene, toluene, or xylene, a halogenated aromatic solvent such as chlorobenzene, dimethylformamide, dimethylacetoamide, N-methylpyrrolidone, dimethylimidazolidinone, or acetonitrile, or tetrahydrofuran, which may be used alone or in a combination of two more mixed solvents.

Also, the reaction may be generally carried out at a reaction pressure of 1 to 200 kg/cm² under an inert atmosphere of nitrogen, argon or carbon dioxide. However, the pressure is preferably in a range of 1 to 150 kg/cm² in terms of the boiling points of the heterocyclic secondary amine of Formula (I) and the solvent, the reaction time, and the reactivity.

The reaction temperature is generally in a range of 15 to 300° C., preferably 50 to 250° C.

The reaction time may vary depending on the catalytic activity, and is in a range of 0.5 to 100 hours, preferably 1 to 30 hours. With respect to processes after completion of the reaction, after removal of the solvent, for example, by distillation, when necessary, the resulting compound may be isolated in a free form or in the form of a mineral acid salt using a method such as distillation under reduced pressure, recrystallization, or chromatography purification.

The MMPP according to the present invention may be used for preventing or treating all types of diseases associated with NF-κB, IKK, and STAT3.

For example, the MMPP may be used to prevent or treat cancers such as lung cancer, gastric cancer, colon cancer, liver cancer, bone cancer, pancreatic cancer, skin cancer, head and neck cancer, skin or intraocular melanoma, liver cancer, uterine cancer, ovarian cancer, rectal cancer, anal cancer, colon cancer, breast cancer, fallopian tube carcinoma, endometrial carcinoma, cervical carcinoma, Hodgkin's disease, esophageal cancer, small bowel cancer, endocrine cancer, thyroid cancer, parathyroid cancer, adrenal gland cancer, soft tissue sarcoma, urethral cancer, penile cancer, prostate cancer, chronic or acute leukemia, lymphocytic lymphoma, bladder cancer, renal or urethral cancer, renal cell carcinoma, prostate cancer, pancreatic cancer, colon cancer, esophageal cancer, head and neck cancer, renal pelvic carcinoma, CNS tumors, primary CNS lymphoma, spinal cord tumors, brainstem glioma, pituitary adenoma, etc.

Also, the MMPP may be applied to various immune diseases, and may, for example, applied to diseases associated with various immune responses, for example, inflammatory diseases such as plasmacytosis, hyperimmunoglobulinemia, anemia, nephritis, cachexia, stock breeder's disease, vascular proliferative nephritis, uveitis, chronic thyroiditis, delayed-type hypersensitivity, Crohn's disease, pancreatitis, arcus idiopathic atrophy, diabetes mellitus, and Alzheimer's disease; autoimmune diseases such as atopic dermatitis, rheumatoid arthritis, osteoarthritis, psoriasis, asthma, graft-versus-host disease, immunodeficiency, systemic lupus erythematosus, and multiple sclerosis; metabolic diseases such as osteoporosis, arteriosclerosis, and myocardial infarction.

In particular, the MMPP of the present invention may have various ensured effects against diseases associated with inflammatory diseases without any side effects caused by direct inhibition of TNF-α, which has been regarded as the drawbacks of the conventional therapeutic agents, by targeting the variety of aforementioned therapeutic agents to treat the diseases and inhibiting the activities of NF-κB, IKK and STAT3 prior to an inflammation expression phase to intrinsically interrupt generation of TNF-α.

Hereinafter, the configurations of the present invention will be described in further detail with reference to embodiments thereof. However, it should be understood that the following embodiments disclosed herein are provided to aid understanding of the present invention, and are not intended to limit the scope of the present invention.

[Example 1] Preparation of 2-methoxy-4-(3-(4-methoxyphenyl)prop-1-en-1-yl)phenol 4-Iodo-2-methoxyphenol (500 mg, 2.0 mmol) and 4-allylanisol (313 mg, 2.0 mmol) were put into a 25 mL flask reactor, and triphenyl phosphine (105 mg, 0.4 mmol), Pd(OAc)$_2$ (44.9 mg, 0.2 mmol), and tributylamine (451 mg, 1.9 mmol) were then added thereto. Thereafter, the resulting mixture was reacted at 45° C. for 2 hours.

The resulting compound was purified through flash silica gel chromatography (hexane/ethyl acetate, 3:1, v/v) to prepare the title compound (119 mg, Yield: 22%) as a dark brown liquid.

High resolution mass spectrometry (HRMS; ESI) m/z [M+H]$^+$ cacld. 271.1329, found 271.1332

$^1$H-NMR: d (CDCl$_3$) 7.32 (d, 2H, J=8.0 Hz), 6.88 (d, 1H, J=9.0 Hz), 6.86 (d, 2H, J=9.0 Hz), 6.76 (d, 1H, J=8.0 Hz), 6.75 (s, 1H), 6.40 (d, 1H, J=16.0 Hz), 6.21 (dt, 1H, J=16.0 Hz, J=6.5 Hz), 5.54 (s, 1H), 3.89 (s, 3H), 3.82 (s, 3H), 3.48 (d, 2H, 7.0 Hz)

The compound according to the present invention can be used to prevent or treat all diseases associated with NF-κB, IKK, and STAT3.

INDUSTRIAL APPLICABILITY

The 2-methoxy-4-(3-(4-methoxyphenyl)prop-1-en-1-yl) phenol according to the present invention can be used to prevent or treat all diseases associated with NF-κB, IKK, and STAT3.

What is claimed is:

1. 2-Methoxy-4-(3-(4-methoxyphenyl)prop-1-en-1-yl) phenol represented by the following Formula 1:

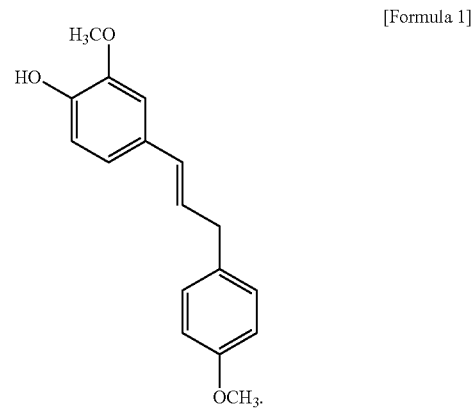 [SMILES: COc1ccc(C/C=C/c2ccc(O)c(OC)c2)cc1]

[Formula 1]

2. A method of preparing 2-methoxy-4-(3-(4-methoxyphenyl)prop-1-en-1-yl)phenol represented by Formula 1, which is prepared by allowing a compound of Formula 2 to react with a compound of Formula 3, as represented by the following Scheme 1:

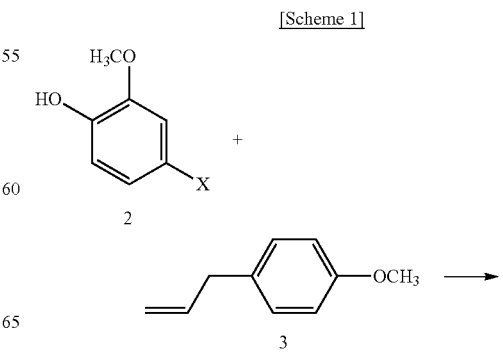

[Scheme 1]

-continued
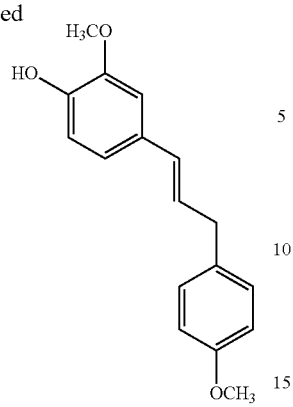
1
wherein X represents a halogen element.
3. The method of claim 2, wherein the X is F, Cl, I, or Br.
4. The method of claim 2, wherein the reaction is carried out in the presence of a palladium catalyst and a base.
5. The method of claim 2, wherein the reaction is carried out by additionally adding a ligand comprising a phosphine or phosphite.
* * * * *